US005222507A

United States Patent [19]
Taylor

[11] Patent Number: 5,222,507
[45] Date of Patent: Jun. 29, 1993

[54] SURGICAL DRAPES AND METHODS OF MAKING SAME

[75] Inventor: Jeffrey L. Taylor, Cincinnati, Ohio

[73] Assignee: Standard Textile Company, Inc., Cincinnati, Ohio

[21] Appl. No.: 680,089

[22] Filed: Apr. 3, 1991

[51] Int. Cl.$^5$ .............................................. A61F 13/00
[52] U.S. Cl. ..................................... 128/849; 128/853
[58] Field of Search ............... 128/846, 849, 852, 853, 128/854, 855, 856

[56] References Cited

U.S. PATENT DOCUMENTS

| | | | |
|---|---|---|---|
| 3,669,106 | 6/1972 | Schrading et al. | 128/853 |
| 4,040,418 | 8/1977 | Collins | 128/852 |
| 4,089,331 | 5/1978 | Hartigan et al. | 128/853 X |
| 4,134,398 | 1/1979 | Scrivens | 128/852 |
| 4,275,720 | 6/1981 | Wichman | 128/853 |
| 4,323,062 | 4/1982 | Canty | 128/852 |
| 4,476,860 | 10/1984 | Collins et al. | 128/852 X |
| 4,616,642 | 10/1986 | Martin et al. | 128/853 |
| 4,957,120 | 9/1990 | Grier-Idris | 128/849 |
| 5,002,070 | 3/1991 | Taylor | 128/853 |
| 5,038,798 | 8/1991 | Dowdy et al. | 128/849 X |

Primary Examiner—Robert A. Hafer
Assistant Examiner—Sam Rimell
Attorney, Agent, or Firm—Kinney & Schenk

[57] ABSTRACT

A surgical drape comprises a main panel and a "critical zone" panel secured thereto. A fenestration is formed by cutting through the "critical zone" panel. The main panel is a light weight fabric having a relatively high coefficient of friction. The "critical zone" panel comprises a barrier panel lying against the main panel and an outwardly facing absorbent panel, having an irregular surface. In an another embodiment, the critical "critical zone" panel is folded to form troughs for capturing liquid incident to a surgical procedure.

16 Claims, 6 Drawing Sheets

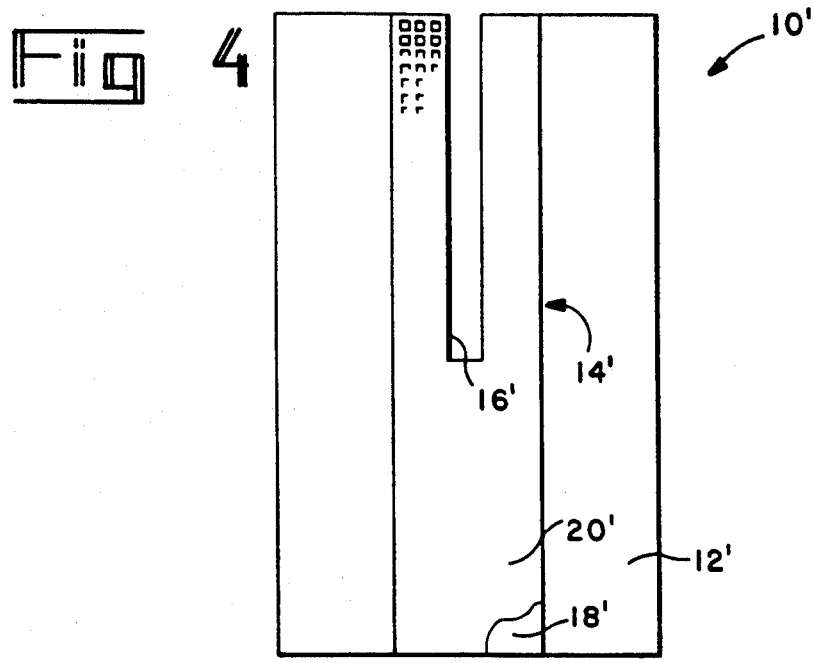
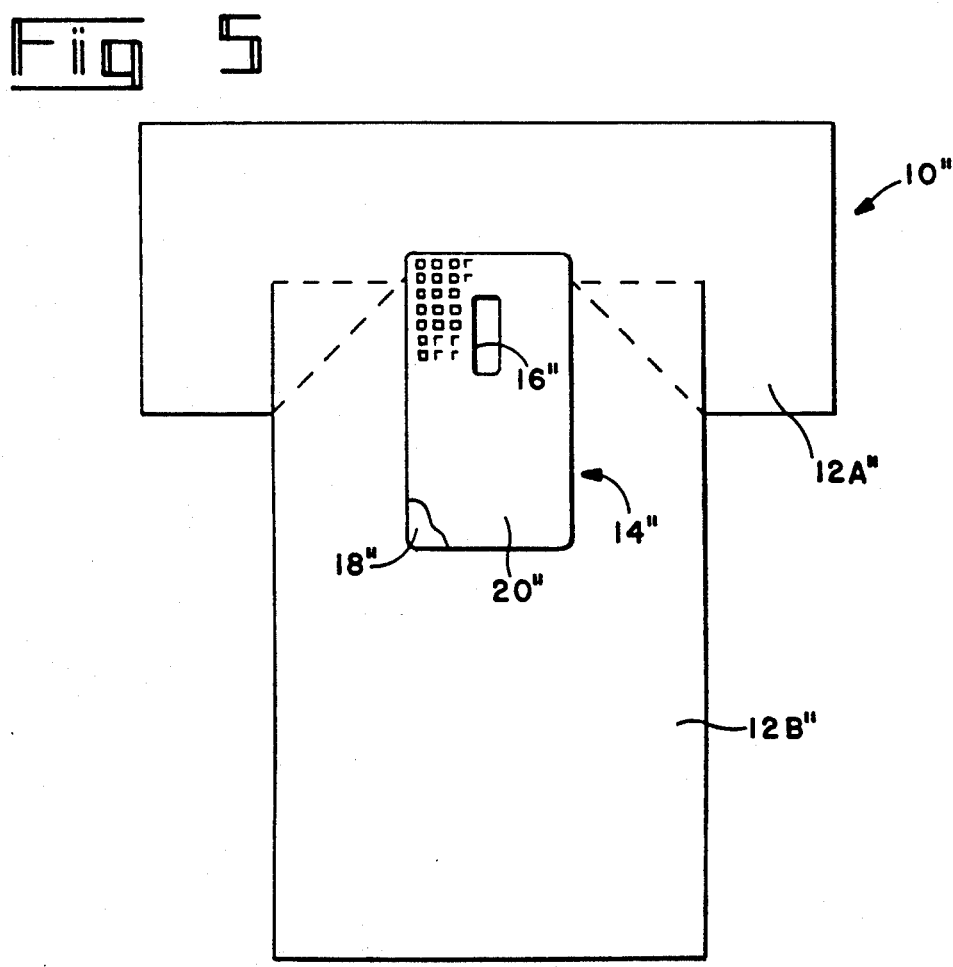

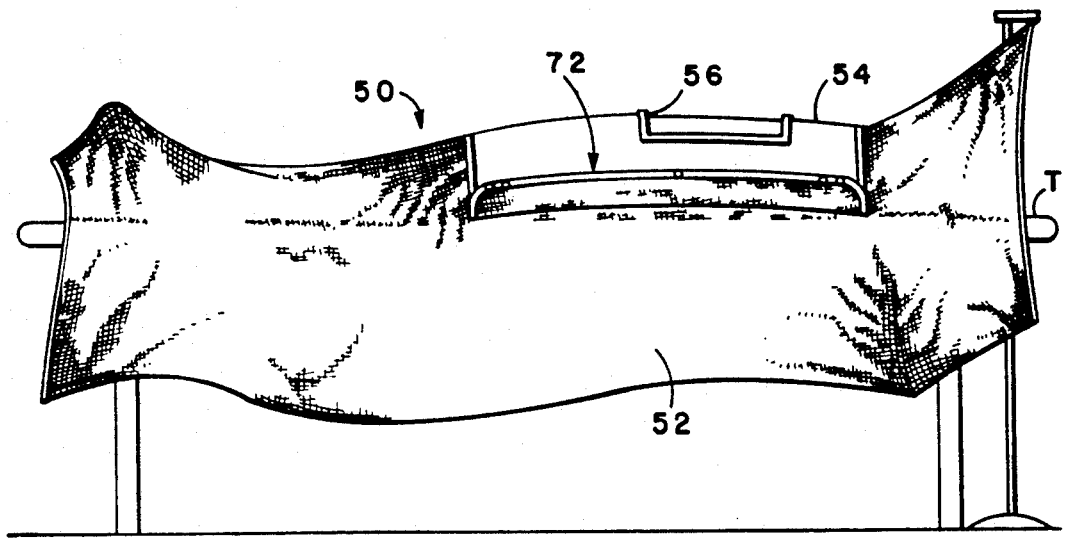
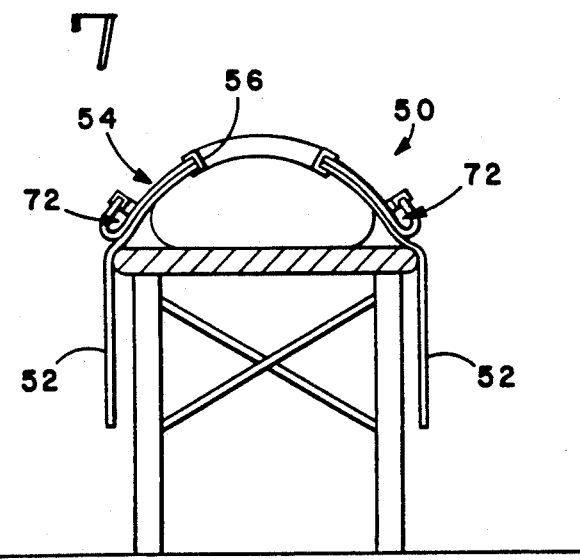

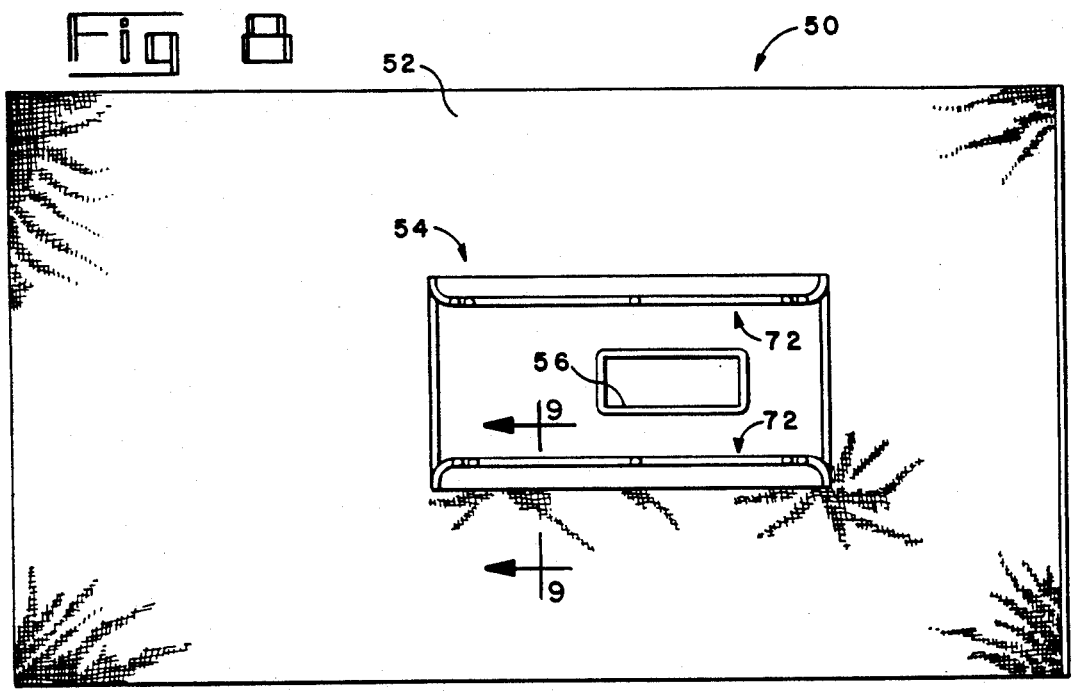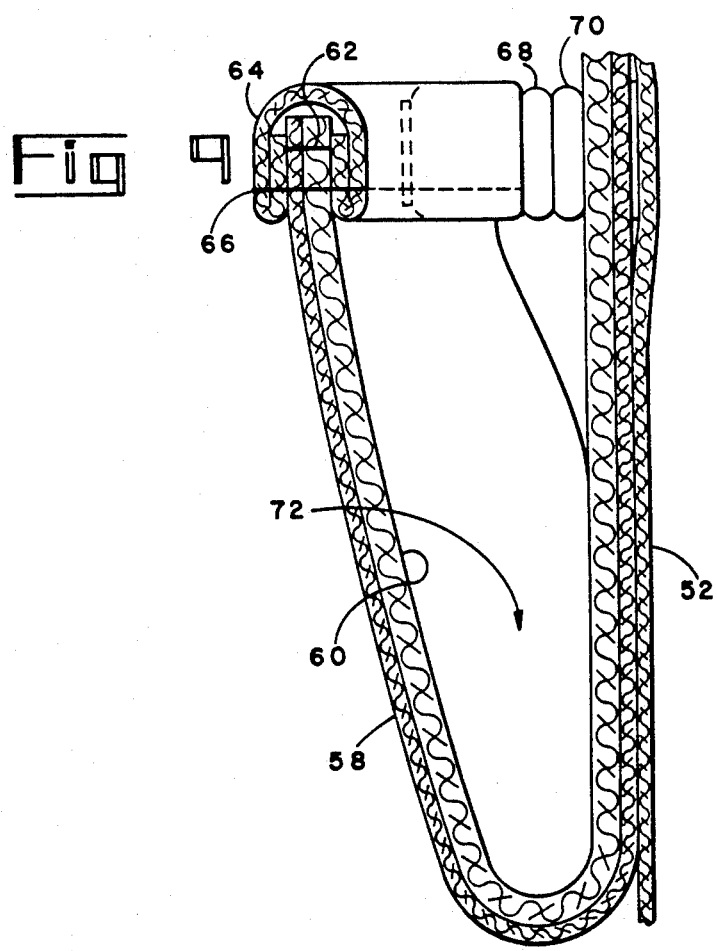

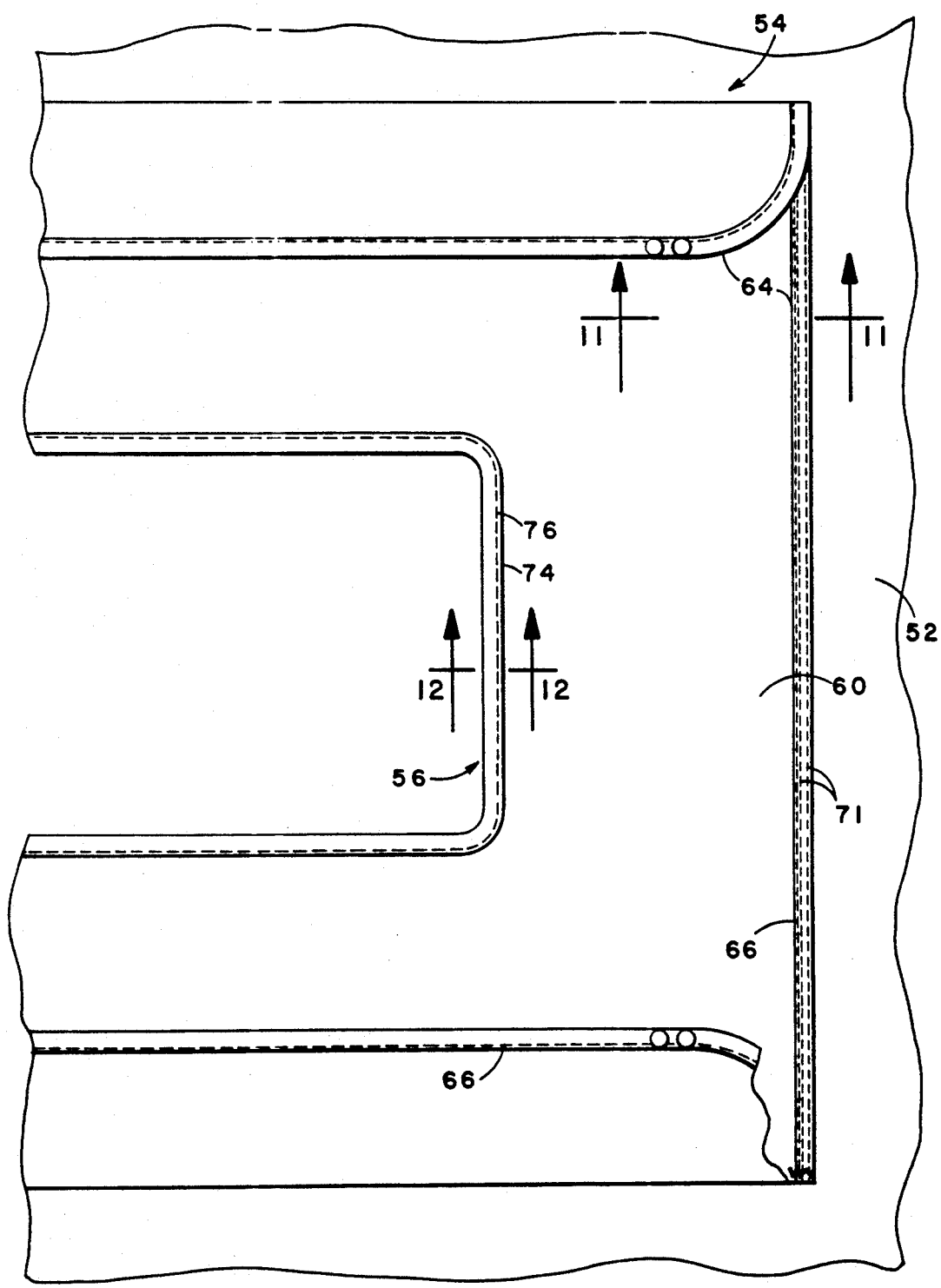

SURGICAL DRAPES AND METHODS OF MAKING SAME

The present invention relates to improvements in surgical drapes.

In the performance of surgical procedures, it is a customary and usual practice to limit the extent to which body liquids, or fluids used in the procedure, will come into contact with the skin surfaces of the patient. One of the reasons for this practice is based on the theory that micro-organisms migrate through a liquid medium instantaneously. Therefore, if there are any micro-organisms on the skin surface of the patent, a surgical drape inhibits their transfer to the surgical site.

To this end clothes are draped over the patient so that only the area immediate adjacent the area of surgical site is exposed. The clothes, or surgical drapes, as they are generally designated, limit contact between the skin surface and blood, or other body liquid, which might exude from an incision. Surgical drapes also limit the extent to which liquids, employed in a procedure, contact the skin surface of a patient.

The use of surgical drapes is more than a matter of general cleanliness and comfort, since body liquids can be the source of infection.

One form of surgical drape, known as a fenestrated shape, comprises an opening, or fenestration, which is registered with the surgical site, usually the skin surface of a patient, where an incision is to be made. It is, of course, essential that the fenestration remain registered with the surgical site throughout the surgical procedure.

These ends, in the past, have been attained by forming the drape from a barrier fabric, which resists penetration by liquids. Both single use and washable, reusable drapes have been used. Generally speaking, reusable materials having the requisite degree of resistance to liquid penetration are relatively expensive and also relatively heavy. It will be briefly noted that reusable drapes are washed, dried and sterilized after each use. Thee procedures tend to degrade the barrier property and limit the number of times such surgical drapes can be used. Per use cost is, thus, a controlling economic factor, being inversely proportional to acquisition cost and the number of times the drape can be reused.

Alternatively, it has been an accepted practice to form the main portion of the drape from alight weight material, such as a percale woven from 50% polyester/50% cotton yarns. The main portion of the drape has a size sufficient for it to be stably positioned relative the surgical site. A second layer of barrier material is then attached to the percale drape, with the fenestration formed in the second layer. The barrier material has a high degree of resistance to liquid penetration and provides protection for the patient in the "critical zone" immediately adjacent to the fenestration. There is little likelihood of body liquids falling onto the drape outside of this "critical zone". Additionally, prior "critical zone" panels have had a contrasting color tog guide a surgeon, or attendant, in limiting contact to the "critical zone". In this fashion, adequate protection is provided for the patient, even though the main portion of the drape provides only limited protection against body liquids striking therethrough.

While prior, reusable, surgical drapes have been marginally adequate for the intended purpose of protecting surgical patients from body liquids, and the like, incident to a surgical procedure, nonetheless, these prior drapes have shortcomings. For example, there is, under certain circumstances, a tendency of the drape to shift relative to the patient. Also, where there is a relatively large volume of body liquids, or liquids incident to the surgical procedure, these liquids can run off of the "critical zone" panel and penetrate the drape to thus contact the skin of the patient. In fact the volume of liquids can be so great that liquids can drop to the floor of the operating room and create a hazard.

Accordingly, the object of the invention is to provide, for a surgical patient, improved protection from body liquids, and/or liquids incident to a surgical procedure coming into contact with the patient's skin.

Phrased differently, the broad object of the present invention is to provide a surgical drape, which gives improved control of body liquids, and other liquids, incident to a surgical procedure.

A related object of the present invention is to attain the foregoing end through the provision of an improved surgical drape which is capable of being washed and sterilized for reuse to the end that it is cost effective.

The foregoing ends are broadly attained by a surgical drape comprising a main panel and a "critical zone" panel secured thereto. The drape has a fenestration bordered by the "critical zone" panel. The "critical zone" panel comprises a barrier panel and an absorbent panel, with the absorbent panel being disposed outwardly of the barrier panel.

At this point it will be noted that the terms "water repellant" and "waterproof" are frequently referenced in connection with the barrier properties of a fabric. The recognized distinction between these terms is that a "waterproof" fabric resists penetration by water under some finite, hydrostatic head. A "water repellant" fabric also resists penetration of water, but only where there is no more than a minimal hydrostatic head, tending to cause penetration of the fabric. Actually, the terms "water repellant" and "waterproof" are misnomers in the present instance, in that many liquids involved in surgical procedures are non-aqueous. According the terms "liquid repellant" and "liquidproof" are used herein, with corresponding meaning.

The main panel of the present drape is, preferably, formed of a light weight, liquid repellent, woven fabric having a relatively high coefficient of friction. The absorbent panel is, preferably, non-piling and non-linting and formed of synthetic yarn. Advantageously, the yarn comprises continuous filament polyester fibers.

The barrier panel is, preferably, a liquid proof fabric. The barrier panel may be a liquid impervious fabric, formed of woven polyester yarns. Such fabrics are breathable, i.e., they are permeable to air and water vapor, it being conventional thinking that breathability is a desirable, if not essential, characteristic for surgical drapes. However, due to the fact that the barrier panel may be formed with a relatively small lateral extent, the barrier fabric may be impervious to both liquids and air and water molecules. The latter type fabric provides advantages in providing a longer service life, with assurance that liquids will not strike therethrough.

It is further preferred that all of the fabrics in the surgical drape have flame resistance and antimicrobial activity properties.

In accordance with the method aspects of the invention, a surgical drape is made by forming a main panel and forming a "critical zone" panel having an area less than the area of the main panel. The "critical zone" is made by securing a barrier panel to an absorbent panel, preferably by stitching. The "critical zone" panel is secured to the main panel, preferably by stitching, with the barrier panel facing the main panel and the absorbent panel facing outwardly. A fenestration is then formed in the drape by cutting through the "critical zone" panel.

Other ends of the invention may be attained by a surgical drape adapted to overlie a patent during the performance of a surgical procedure and having a fenestration for registration with the site of a surgical procedure. The drape comprises a main panel of relatively large lateral extent and a "critical zone" panel of substantially smaller lateral extent and extending outwardly from said fenestration.

This drape is characterized in that the "critical zone" panel comprises a liquid prof, barrier panel, and a trough disposed outwardly of the fenestration and adapted to receive liquids incident to a surgical procedure. In a more specific sense, a marginal edge portion of the barrier panel is folded on itself to form this trough.

The above and other related objects and features of the invention will be apparent from a reading of the following description of preferred embodiments of the invention, and the novelty thereof pointed out in the appended claims.

IN THE DRAWINGS

FIG. 4 is a plan view of another embodiment of the present invention; and

FIG. 5 is a plan view of yet another embodiment of the present invention;

FIG. 6 is a view of an a surgical drape, which embodies further features of the invention, illustrating the surgical drape as it would be draped over a patient;

FIG. 7 is a section taken on line 7—7 in FIG. 6;

FIG. 8 is a plan view of the surgical drape seen in FIG. 6;

FIG. 9 is a section, on a greatly enlarged scale, taken on line 9—9 in FIG. 8;

FIG. 10 is a plan view, on an enlarged scale, of the critical zone of the surgical drape, as seen in FIG. 8;

Figure 1:
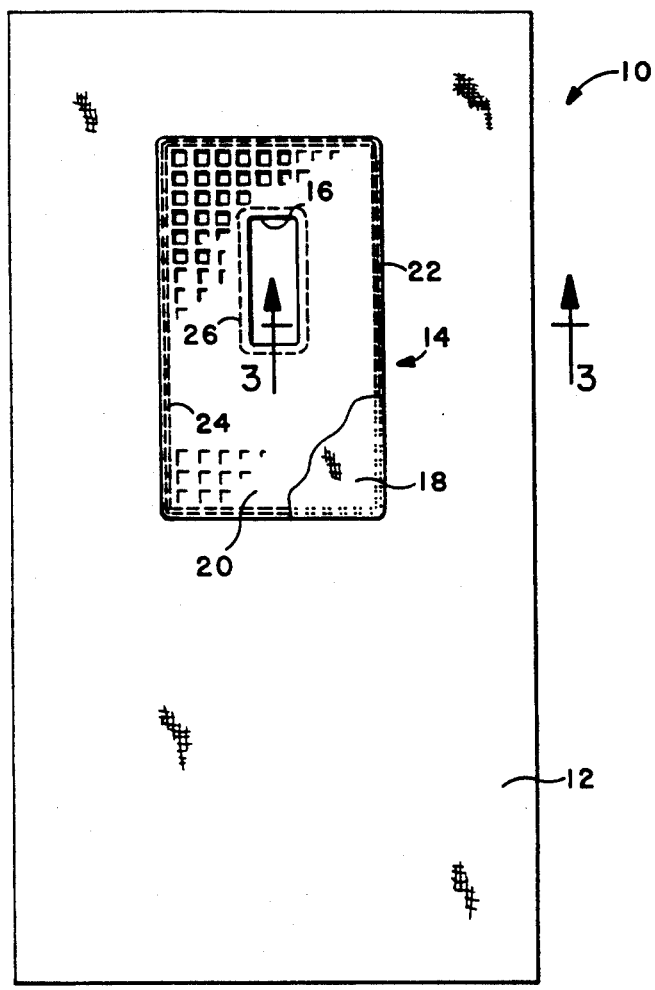
FIG. 1 is a plan view of a surgical drape embodying the present invention.

FIG. 1 illustrates a surgical drape 10 of a type suitable for laparotomy and laminectomy operations. The drape 10 comprises a main panel 12, and a compositely formed "critical zone" panel 14. A fenestration, or window, 16 is formed in the drape 10 within the outline of the "critical zone" panel 12. In use the drape 10 is laid draped over the body of a patient with the lower side of the main panel 10 in contact therewith. The drape 10 is then shifted in a manner to bring the fenestration 16 into registration with the location where an incision is to be made, i.e., the surgical site.

Figure 2:
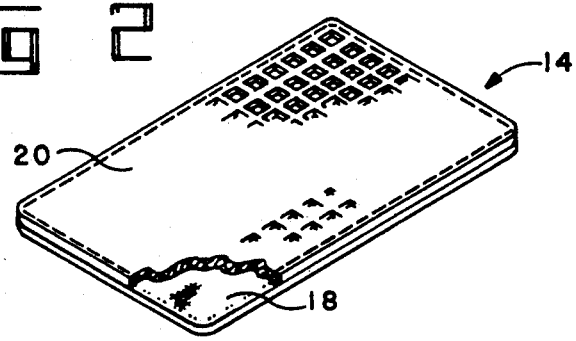
FIG. 2 is a perspective view of a subassembly employed in fabricating the surgical drape seen in FIG. 1.
Figure 3:
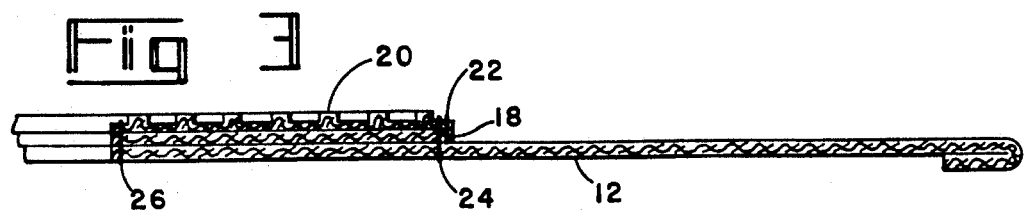
FIG. 3 is a section, on an enlarged scaled, taken on line 3—3 in FIG. 1, with the thickness of cloth layers greatly exaggerated.

The "critical zone" panel 14 comprises a barrier panel 18 and an absorbent panel 20. Advantageously, the panels 18 and 20 are first secured together as a subassembly, FIG. 2, by stitching 22 peripherally of their marginally edges. This subassembly may then be placed on the main panel 12 and secured thereto by stitching 24. Thereafter, the enestration 16 may be formed, as by die cutting the fabric layers, 12, 18 and 20. Preferably, the edge portions of these layers, marginally of the fenestration 16 are then bound together by stitching 26. The marginal edges of the main panel 12 may also be seamed, or hemmed, as indicated in FIG. 3.

The main panel 12 is formed of a woven fabric which has characteristics which make it particularly effective in protecting the patient during a surgical procedure.

Thus, the material of panel 12 is highly flexible with a relatively light weight, in the order of 4.0 ounce per square yard. The flexible characteristic facilitates the drape 10 to conform to the contour of a person's body so that the fenestration 16 may be readily shifted to the surgical site, and then remain in registration with the surgical site as the surgical procedure is performed. The light weight characteristic, among other things means a lower volume, or mass, for the surgical Another characteristic of the fabric for panel 12 is that it has a relatively high coefficient of friction. This characteristic further assists in preventing the drape from inadvertently shifting relative to the body of the patient, to the end that the fenestration 16 is maintained in registration with the site of the incision.

A preferred fabric for the main panel 12 is described in copending U.S. patent application Ser. No. 679,775, filed Apr. 3, 1991, in the names of Jeffrey L. Taylor, John M. Smith and C. Dean Goad. Briefly this fabric may be characteristic as a synthetic yarn fabric having a "hand" which is essentially the same as the "hand" of cotton muslin. This synthetic yarn fabric provides several advantages over cotton muslin, and the above referenced percale fabric, both of which have been used in fabricating reusable surgical drapes. "Hand" includes the flexibility of the fabric, which facilitates its ability to be draped over and conform to the contours of a patient.

These advantages include non-linting and non-pilling, which eliminate a potential source of contamination in the operating arena.

The preferred fabric is further characterized in that it is woven with a wave which creates floats and by the floats comprising air texturized, core and effect, polyester yarns. More specifically, the it is preferred that the main panel fabric be a two by two twill in which the filling yarn are air texturized, core and effect yarns and the warp yarns are false twist texturized yarns, both of the warp yarns and filling yarns are set yarns to provide dimensional stability.

The described fabric construction, and particularly the air texturized, core and effect yarn provides the desired coefficient of friction for the main panel 12. It is also to be noted that coefficient of friction is also a factor, or characteristic, of the desired "hand" of the main panel 12, such characteristic being gauged against cotton muslin.

It is further preferred that the main panel be liquid repellant (reference the discussion of this term above). Polyester (or equivalent synthetic materials, such as nylon) are hydrophobic, This hydrophobic property provides inherent water repellency. Additionally, the above referenced application, provides teachings of the use of finish treatments which enhance to the water repellency of the fabric.

Further characteristics of the fabric of panel 12 are that it has a relatively high strength, it creates little or no lint, either in use or in washing, and that its functionally characteristics are not unduly degraded by repeated washing/steralization cycles. These characteristics contribute to an improved cost of the present surgical drape, on a per use basis, even though its acquisition cost may exceed that of conventional surgical drapes.

As its name implies, the function of the barrier panel 18 is to provide a high resistance to liquid penetration in the "critical zone" marginally of the fenestration 16. The barrier panel 18 is formed of a liquid proof fabric, in contrast to the water repellent fabric forming the main panel 12. Additional characteristics of the barrier panel 18 flexibility, or a "hand", which permits the "critical zone" portion of the drape to conform to the contour of the patient the surgical site. Further the panel should be lint free and non-pilling to prevent the intropanel should be lint free and non-pilling to prevent the introduction of this type of contaminant in the surgical arena. Importantly, the fabric for the barrier panel is capable of being repeatedly washed, dried and sterilized using known institutional processes, which employ harsh etergents and involve high temperatures, all without any serious degradation of the noted characteristics.

It has been noted, in prior art teachings, that there is a need for a surgical drape to be "breathable", i.e., to permit the passage of air and/or water vapor therethrough. While there are known barrier fabrics which provide both liquid impermeability and "breathability", one function is, to a greater or lesser extent, inversely proportional to the other. By providing the a "critical zone" panel, it is possible to employ barrier fabrics which have increased resistance to liquid penetration, since the main panel 12 provides breathability for the remainder of the drape.

Thus, the fabric for the barrier panel 18 may be selected primarily for its liquid impervious characteristic. A preferred fabric for this purpose is disclosed in copending application Ser. No. 679,735, filed Apr. 3, 1991, in the names of Jeffrey L. Taylor, Roy Luckenbach and Michael Coco. The referenced fabric is generally characterized by a silicone membrane having a thickness of 0.002–0.010 inches, which is bonded to a tightly woven, polyester fabric substrate. Such fabrics, having a weight in the range of approximately 6–7 ounces per square yard have the desired "hand".

An alternate fabric for the barrier panel 18 is taught in U.S. Pat. No. 4,822,667. That fabric is a tightly woven polyester which enable it to have the desired resistance to liquid penetration after as many as 100 washing/sterilization cycles.

The primary characteristic of the absorbent panel 20 is its ability to absorb liquids. It is further preferred that the panel 20 be non-pilling and non-linting after 100 cycles of washing/sterilization. These characteristics may be provided by making the fabric for panel 20 of yarns (knitted or woven), each comprised of a plurality of continuous filaments made of synthetic resinous (plastic) material, preferably polyester, and treating the layer to impart hydrophilic properties thereto. Commercially available hydrophilic finishes may be used to treat the fabric 20 in order to obtain the desired absorbency property.

A further characteristic of the absorbent panel 20 is that it is provided with an irregular surface. This, irregular surface, bordering the fenestration 16, is of great convenience to a surgeon, in that he may temporarily place an instrument on the "critical zone" panel, with little or no danger of it slipping off the drape. Thus, it is preferred that the absorbent panel 20 have what is referenced, in the textile art, as a texturized surface. FIGS. 2 and 3 illustrate the use of a texturized surface in the form of a waffle pattern. Waffle weaves are well known in the textile art and take various forms suitable for the absorbent panel 20, all as will be readily apparent to one skilled in the art. Texturized knit, or woven constructions enhance the absorbency of the panel 20 and, for this further reason, are preferred.

Preferred fabrics for the layer 20 are disclosed, and more particularly described in application for U.S. patent Ser. No. 548,136, filed Jul. 5, 1990.

As indicated above, the surgical drape 10 is placed on a patient, positioned on an operating table. The drape is positioned so that the fenestration 16 is located at the point where an incision is to be made. Drape 10 is designed for use in laparotomy procedures an would be draped over a patients torso, with the fenestration registered with the main trunk of the patient. The relatively high coefficient of friction property of the main panel 12 facilitates initial positioning of the drape and then maintains the fenestration in registration with the incision during the laparotomy procedure.

In the normal case, liquids which might exude, or be splashed, from the incision or which might drop from the instruments employed in the procedure, outside of the fenestration 16, fall upon and are absorbed by he absorbent panel 20, of the "critical zone" panel 14. This provides a highly effective means for controlling undesired flow of body liquids or the like. The absorbent panel 20 serves in the nature of a reservoir. The barrier panel 18, then serves to prevent the liquid absorbed into the panel 20 from penetrating through the drape 10 and contacting the skin of the patient.

Body liquids, or the like, which might fall outside the "critical zone" panel 14 are, in most instances, minimal in amount and the medium barrier properties of the main panel 12 are sufficient to protect the patient.

As indicated, the various components of the surgical drape 10 are capable of being washed and sterilized for subsequent reuse. Thus, the present drape is not only highly efficient in protecting the patient, but is also cost effective.

The fabrics forming the main panel 12, the barrier panel 18 and the absorbent panel 20 also, preferably, have slow burn rates and antimicrobial activity characteristics.

Burn rate standards are established by the Federal Consumer Products Safety Commission. The fabrics of the drape 10 meet the criteria for Class 1, as set forth in 16 CFR 1610.40, revised as of Jan. 1, 1986, both initially (when first placed in service) and after 100 washing/sterilization cycles.

Antimicrobial activity is assessed using CTM-0923. The fabrics of the drape 10 have antimicrobial activity such that, initially, there is no growth and at least a 90% kill and no growth after 100 washing/sterilization cycles.

Flame resistance and antimicrobial and static electricity dissipation properties can be provided by techniques known in the art and/or are taught by the disclosures in the referenced patent and/or patent application.

FIG. 4 illustrate a "split" surgical drape 10'. The drape 10' comprises the same components as in the first embodiment, which components are identified by primed reference characters. The drape 10' differs in that the fenestration 16' extends to the upper edge thereof. This permits the drape 10', for example, to be placed on opposite sides of a patient's neck, where the operative procedure is in that area.

Fabrication of the drape 10' may be the same as in the previous embodiment, employing the same fabrics, respectively, for the main panel 12', barrier panel 18' and absorbent panel 20'. The latter two panels may be first sewed together as a "critical zone" panel 14' subassembly and then mounted on the main 12' and the fenestration 16' die cut and seamed. It will be noted that the "critical zone" panel 14' extends for the full length of the main panel 12'. This configuration of the "critical zone" panel 14' is selected because it is to be anticipated that body liquids may fall onto this area of the drape 10' in the types of procedures for which a "split" surgical drape is employed.

FIG. 5 illustrates a winged laparotomy drape 10". The drape 10" comprises the same basic components as the drape 10, which components are identified by the same reference characters, double primed. This drape differs in that the main panel is compositely formed by panels 12A" and 12B". The surgical drape 10" covers the arms of the patient that are positioned perpendicular to the body of the patient, normally for the convenience of the anesthesiologist, who is administering anesthesia during the surgical procedure.

The "critical zone" panel 14", comprising barrier panel 18" and absorbent panel 20", may, again, be formed as a subassembly and mounted on the main panels 12A" and 12B" in the fashion above described, with the fenestration 16" then being formed with the minimum opening to provide access for the performance of the particular surgical procedure for which the drape 10" is intended.

The foregoing embodiment are highly effective in attaining the ends of the present invention. However, there are surgical procedures and circumstances, where the volume of liquids can exceed the absorption capacity of the absorbent panel 20. This is to say that, while not capable of being precisely defined, there is a practical limit on the size, or lateral extent of the "critical zone" panel 14. The ends of minimizing cost and overall weight dictate the size of the "critical zone" panel 14 be relatively small, and one skilled in the art will appreciate when the size of the "critical zone" panel becomes too great for such purposes.

In any event, the embodiment of FIGS. 6-12, serves the end of maintaining a minimum size "critical zone" panel, which providing means for controlling large volumes of liquid during the performance of a surgical procedure.

The surgical drape of this embodiment, identified generally by reference character 50 (FIG. 8) is designed for laparotomy procedures. This surgical drape comprises the same basic elements as found in the previous embodiments, thus there is a rectangular main panel 52, and a compositely formed "critical zone" pane 54. A fenestration 56 is formed in the drape 50 within the outline of the "critical zone" panel 54.

Figure 11:
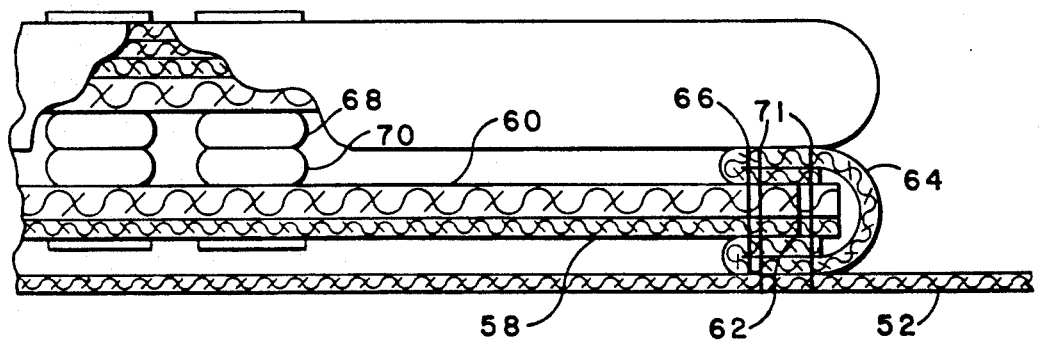
FIG. 11 is a section, on a further enlarged scale, taken on line 11—11 in FIG. 10.
Figure 12:
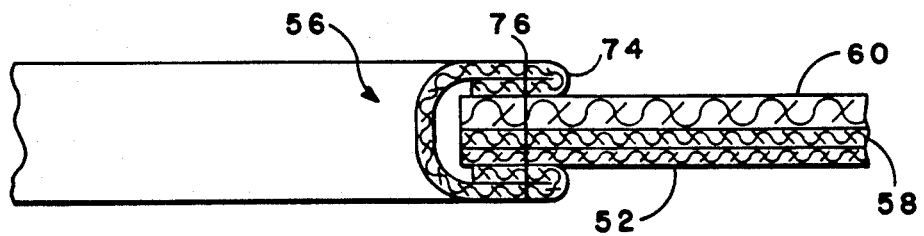
FIG. 12 is a section, on a further enlarged scale, taken on line 12—12 in FIG. 10.

The "critical zone" panel comprises a barrier panel 58 and an absorbent panel 60 (FIGS. 9, 11 and 12). These panels may be secured together by stitching 62 which extends marginally of the peripheries of the panels 58, 60. The peripheries of these panels may then be edge bound by a bias tape 64, secured by stitching 66. Additionally, snaps 68 are secured along opposite edges of the "critical zone" panel 54. A second set of snaps 70 is secured to the "critical zone" panel 54, inwardly of and in aligned reaction with the snaps 68. These snaps are well known and commercially available. One set of snaps, 68 or 70 is a male snap and the other set is a female set. Their method of attachment, as by upsetting a metal tube, is also well known. As will be apparent, the snaps 68, 70 may be pressed together to provide a connection therebetween. A simple tension forces permits the snaps to be disengaged.

When the snaps are engaged, as illustrated in the drawings, opposite marginal edge portions of the "critical zone" panel 54 are folded inwardly to form troughs 72.

The described subassembly, comprising panels 58, 60, may then be secured to the main panel 52 by stitching 70 which extends marginally of the opposite ends of the "critical zone" panel 54 and terminates, approximately, at the bottom of the trough 72, which is formed when the snaps 68, 70 are engaged. Bar tacking, or similar means, may be provided at the opposite ends of the stitching 70.

After the "critical zone" panel 54 is thus secured to the main panel 52, the panels 52, 58 and 60 may be die cut to form the fenestration 56. The portions of the panels defining the fenestration opening may then be edge bound by a tape 74, secured by stitching 76 (FIG. 12).

At this point it will be noted that selection of the fabrics for the main panel 52, barrier panel 58 and absorbent panel 60 is controlled by the same considerations detailed in connection with the corresponding main panel 12, barrier panel 18 and absorbent panel 20, found in the first described embodiment. These is to say that the corresponding panels provide the same basic functions in both embodiments. It will be noted that the outer surface of the absorbent panel 60 is not illustrated as having a waffle pattern. This is simply to indicate, more generally, that this surface may be texturized, in various ways to provide increased friction and absorbency.

FIGS. 6 and 7 further illustrate the use of the surgical drape 50, showing it disposed, in conventional fashion, over a patient positioned on an operating table T. The fenestration 56 is registered with the surgical site for performance of a laparotomy procedure. It will be seen that the surgical drape 50 folds downwardly to position the troughs 72 in an angled, upwardly open orientation.

Thus any liquids, incident to the procedure, which exceed the absorption capacity of the panel 60, will collect in the trough. If the amount of liquid is not excessive, the liquid will simply be collected in the trough and not fall to the floor, where it could be a hazard. If the volume of liquid is sufficiently great, a nurse can insert a suction tube into the trough 72 and remove the liquid to thereby prevent it from draining to the floor.

It will also be seen that the troughs 72 provide a further means for the control of surgical instruments. Thus, if for some reason, an instrument would slip from the generally horizontal portion of the "critical zone" panel 54, despite the increased friction of the absorbent panel 60, it will, in most cases, be trapped in one or the other of the troughs 72.

It is to be noted that the snaps 68, 70 space the side edge portions of the "critical zone" panel 54 from the main portion thereof, thereby creating a finite opening for the troughs 72. It is to be further noted, from FIG. 9, that there is a tendency of the marginal edge portions of the "critical zone" panel 54 to bulge outwardly, thereby increasing the opening of the troughs 72. These features facilitate the insertion of a suction tube to remove excess liquid, as well as enhancing the chances that a surgical instrument will be caught in the troughs, rather than falling to the floor.

It has been found that the foregoing ends are best attained by the illustrated provision of a pair of mating snaps 68, 70, adjacent each end of the trough, and a single mating snaps 68, 70 centrally thereof.

As an alternate to the described provision of an open ended trough, the ends of the trough could be closed. This would provide the advantage of eliminating the need for suctioning off liquid during a procedure, or, at least, minimizing the frequency of suctioning off liquid.

However, the describedse of releasable means to form the trough is preferred. The basis for this preference is that the "critical zone" panel 54 can be placed in a flat condition for washing/sterilization. Thus, after use, the snaps 68, 70 are disconnected before the washing/sterilization processes. In this fashion, possible entrapment of solid matter, which would also fall into a trough during a surgical procedure, is eliminated. The elimination of the troughs, in this fashion, therefore, gives a greater assurance that the surgical drape can be effectively recycled for use in a subsequent surgical procedure, through the use of existing washing/sterilization techniques.

It is also to be recognized, that the provision of troughs provides an alternate approach to controlling liquids incident to a surgical procedure. While the use of this feature is preferred in combination with an absorbent panel, it would be possible to obtain some advantages by eliminating the absorbent panel as a component of the "critical zone" panel 54. Alternatively, the absorbent panel need not be coextensive with the barrier panel of the "critical zone" panel 54 and could be provided only in the areas immediately adjacent to the fenestration 56.

These and other variations from the embodiments herein disclosed will occur to those skilled in the art within the spirit and scope of the present invention as set forth in the following claims.

Having thus described the invention, what is claimed as novel and desired to be secured by Letters Patent of the United States is:

1. A reusable surgical drape comprising
   a liquid repellant main panel and
   a "critical zone" panel secured to the upper surface of the main panel,
   said drape having a fenestration bordered by the "critical zone" panel,
   said "critical zone" panel comparing
   a liquid proof, barrier panel, and
   an absorbent panel overlying the barrier panel,
   the main panel, barrier PANEL and absorbent panel being formed of 100% synthetic textile fabrics, characterized by a flexible "hand" which facilitates their ability to drape and conform to the body configuration of a patient, and wherein
   the main panel is formed of a light weight fabric having a relatively high coefficient of friction sufficient to prevent inadvertent shifting of the surgical drape relative to a patient and thereby maintain the fenestration in registered relation to a surgical site, further characterized in that
   the main panel fabric is a woven polyester yarn fabric comparing core and effect texturized yarns, which provide the relatively high coefficient of friction.

2. A surgical drape as in claim 1 further characterized in that
   the main panel fabric is a twill woven fabric.

3. A surgical drape as in claim 2 further characterized in that
   the warp yarns of the main panel fabric are false twist texturized yarns and the filling yarns are air textured core and effect yarns.

4. A surgical drape as in claim 1 further characterized in that
   the barrier panel is a breathable, woven fabric formed of a synthetic yarn and has a high resistance to liquid penetration after repeated washing/sterilization cycles.

5. A surgical drape as in claim 1 further characterized in that
   the barrier panel comprises a liquid impervious membrane and a supporting fabric substrate.

6. A surgical drape as in claim 1 further characterized in that
   the absorbent panel is non-pilling and non-linting and is formed of synthetic yarn comprising continuous filaments.

7. A surgical drape as in claim 1 further characterized in that
   the absorbent panel
   is formed of continuous filament polyester yarn and
   has an, irregular texturzied, upper surface, which provides a relatively high coefficient of friction for retaining surgical instruments thereon.

8. A surgical drape as in claim 1 further characterized in that
   the barrier panel is a breathable, woven fabric formed of a synthetic yarn and has a high resistance to liquid penetration after repeated washing/sterilization cycles.

9. A surgical drape as in claim 1 further characterized in that
   the barrier panel comprises a liquid impervious membrane and a supporting fabric substrate.

10. A reusable, surgical drape adapted to overlie a patient during the performance of a surgical procedure and having a fenestration for registration with the site of a surgical procedure,
    said drape comprising
    a main panel of a given lateral extent,
    a "critical zone" panel of substantially smaller lateral extent and extending outwardly from said fenestration,
    wherein
    the "critical zone" panel comprises
    a liquid proof, barrier panel, and
    characterized in that
    a marginal edge portion of the barrier panel is folded on itself to define a bottom, folded portion, said marginal edge portion being in spaced relation to the main portion of the barrier panel and forms an upwardly open, non-filled trough of substantial depth, extending upwardly from the bottom folded portion, for the reception therein of liquids incipient to the performance of a surgical procedure, as well as to trap surgical instruments, or the like which might slip from a position on the "critical zone" panel adjacent the fenestration, and means are provided for spacing, the edge of the said marginal edge portions from the main portion of the barrier panel, to define a spaced opening for said non-filled trough, further characterized in that means for releasably securing said marginal edge portion of the barrier panel to the main portion of the barrier panel, whereby the surgical drape may be washed and sterilized with the barrier panel in an unfolded condition.

11. A surgical drape as in claim 10 further characterized in by snap means for releasably securing said marginal edge portion of the barrier panel to the barrier panel and spacing the edge thereof from the main portion of the barrier panel.

12. A surgical drape as in claim 10 further characterized in that the main panel is generally rectangular and has side portions adapted to drape beneath the level of an operating table on which a patient is positioned, the "critical zone" panel is also generally rectangular and has side portions generally parallel with the side portions of the main panel, said "critical zone" panel extends outwardly on opposite sides of the fenestration to a point where both are angled from a horizontal plane, when the surgical draped is draped over a patient, and further characterized in that the marginal edge portion of the opposite side of the barrier panel is folded on itself to define a second, bottom, folded portion, said marginal edge portion of the opposite side being in spaced relation to the main portion of the barrier panel and forming a second upwardly open, non-filled trough of substantial depth for the reception therein of liquids incident to the performance of a surgical procedure and means are provided for spacing, the edge of the said marginal edge portions from the main portion of the barrier panel, to define a spaced opening for said non-filled trough, further characterized by means for releasably securing said marginal edge portion of the barrier panel to the main portion of the barrier panel, whereby the surgical drape may be washed and sterilized with the barrier panel in an unfolded condition.

13. A surgical drape as in claim 12 further characterized in that the "critical zone" panel further comprises an absorbent panel, which overlies the barrier panel and forms the outer surface of the "critical zone" panel.

14. A surgical drape as in claim 12 further characterized in that the "critical zone" panel is in a single layer between said troughs and is secured to the main panel by stitch extending marginally of its ends and terminating adjacent said troughs.

15. A surgical drape as in claim 9 further characterized in that the "critical zone" panel has a color which contrasts with the color of the main panel.

16. A surgical drape as in claim 1 further characterized in that the absorbent panel of the "critical zone" panel has a contrasting color.

* * * * *